US012688939B2

(12) United States Patent
Mande et al.

(10) Patent No.: US 12,688,939 B2
(45) Date of Patent: ***Jul. 21, 2026

(54) SYSTEM AND METHOD FOR RISK ASSESSMENT OF PARKINSONS DISEASE

(71) Applicant: Tata Consultancy Services Limited, Mumbai (IN)

(72) Inventors: Sharmila Shekhar Mande, Pune (IN); Chandrani Bose, Pune (IN); Harrisham Kaur, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1124 days.

This patent is subject to a terminal disclaimer.

(21) Appl. No.: 17/632,800

(22) PCT Filed: Aug. 5, 2020

(86) PCT No.: PCT/IB2020/057391

§ 371 (c)(1),
(2) Date: Feb. 4, 2022

(87) PCT Pub. No.: WO2021/024195

PCT Pub. Date: Feb. 11, 2021

(65) Prior Publication Data

US 2022/0293277 A1     Sep. 15, 2022

(30) Foreign Application Priority Data

Aug. 5, 2019    (IN) .............................. 201921031558

(51) Int. Cl.
| | |
|---|---|
| *G16H 50/30* | (2018.01) |
| *C12N 15/10* | (2006.01) |
| *C12Q 1/6869* | (2018.01) |
| *G16B 20/00* | (2019.01) |
| *G16B 40/00* | (2019.01) |
| *G16H 50/20* | (2018.01) |

(52) U.S. Cl.
CPC ......... *G16H 50/30* (2018.01); *C12N 15/1003* (2013.01); *C12Q 1/6869* (2013.01); *G16B 20/00* (2019.02); *G16B 40/00* (2019.02); *G16H 50/20* (2018.01); *C12N 2320/10* (2013.01)

(58) Field of Classification Search
None
See application file for complete search history.

(56) References Cited

U.S. PATENT DOCUMENTS

| | | |
|---|---|---|
| 2014/0179726 A1 | 6/2014 | Bajaj et al. |
| 2018/0196044 A1 | 7/2018 | Mazmanian et al. |
| 2022/0293217 A1* | 9/2022 | Mande ................... G16B 20/00 |

FOREIGN PATENT DOCUMENTS

WO      WO 2017/044886 A1     3/2017

OTHER PUBLICATIONS

Dovrolis N. Computational profiling of the gut-brain axis: microflora dysbiosis insights into neurological disorders. Briefings in Bioinformatics 20(3): 825-841. (Year: 2017).*
International Search Report for PCT/IB2020/057391, mailed Mar. 12, 2021.
Martin et al., "The Brain-Gut-Microbiome Axis," Cellular and Molecular Gastroenterology and Hepatology, 6(2):133-148 (2018).
Written Opinion of the International Searching Authority for PCT/IB2020/057391, mailed Mar. 12, 2021.

\* cited by examiner

*Primary Examiner* — Olivia M. Wise
*Assistant Examiner* — Robert J. Kallal
(74) *Attorney, Agent, or Firm* — Finnegan, Henderson, Farabow, Garrett & Dunner, LLP

(57)     ABSTRACT

The onset of Parkinson's disease (PD) is a serious concern for elderly people and it is necessary to identify the risk for PD in an individual as early as possible. A system and method for risk assessment of an individual for Parkinson's disease (PD) has been provided. The system is using a non-invasive method for risk assessment of PD through prediction of metabolic potential of the bacteria residing in gastrointestinal tract of the individual. The system 100 is configured to calculate a score, which is evaluated from the gut bacterial taxonomic abundance profile, which is indicative of its metabolic potential for production of a particular neuroactive compound. This score is subsequently used to assess the risk of an individual of being affected by PD. Further, the present disclosure also provides microbiome based therapeutic approaches that can potentially minimize the side effects through maintaining the healthy cohort of bacteria in gut.

12 Claims, 4 Drawing Sheets

SYSTEM AND METHOD FOR RISK ASSESSMENT OF PARKINSONS DISEASE

PRIORITY CLAIM

This application is an US National Stage Filing and claims priority from International Application No. PCT/IB2020/057391, filed on Aug. 5, 2020, which application claims priority from Indian Provisional Patent Application No. 201921031558, filed on Aug. 5, 2019. The entire contents of the aforementioned application are incorporated herein by reference.

TECHNICAL FIELD

The embodiments herein generally relate to the field of Parkinson's disease, and, more particularly, to a method and system for assessing the risk of an individual for Parkinson's disease using the metabolic potential of the resident gut bacteria.

BACKGROUND

Parkinson's disease (PD) or Parkinson's syndrome is a progressive neurodegenerative disorder that primarily affects dopamine producing neurons ('dopaminergic' neurons). According to a global estimate, around 6.1 million people are affected with the disease. Majority of patients develop the disease at around the age of 60. However, about 5-10% of people experience 'early-onset' of the disease, where the symptoms begin before the age of 50. The symptoms are diverse and vary significantly among individuals. Some of the primary symptoms include tremor, slow movement, limb rigidity, balance and posture impairment, and speech and writing abnormalities. It is believed that the disease causing factors are combinations of genetic and environmental factors (like toxins). Although some of the causes of the functional impairment that occur in PD are known, many remain to be understood. Besides damage in dopaminergic neurons, other causes include loss of the nerve endings that produce norepinephrine (involved in many automatic body functions, such as, blood pressure, heart rate, etc.), formation of 'Lewy bodies' (unusual clumps) in brain cells, etc.

At present, no therapies are available for curing the disease, but medicines, surgeries and other therapies are recommended for relieving the symptoms of Parkinson's disease. Diagnosis of Parkinson's disease is performed based on neurological examination and medical history. In addition, single-photon emission computerized tomography (SPECT) scan, which is a dopamine transporter (DAT) scan, may be suggested to the patient. This scan sometimes help in the diagnosis, but cannot be considered as a confirmatory test for the same. Apart from these, blood tests and imaging tests (such as ultrasound of the brain, MRI, CT, and PET scans) are recommended for ruling out other diseases/disorders. The doctor may also suggest medication with drugs of PD (such as levodopa, carbidopa) in order to diagnose the disease based on the patient's response to the drug. Unfortunately, no laboratory test is currently available for conclusive diagnosis of the disease. Diagnosing the disease at its initial stage is difficult since the early symptoms are often misrecognized as effects of normal ageing. Thus proper diagnosis happens at a stage when substantial amount of neurons have already been impaired or lost. Similarity of the early symptoms of PD with the signs of normal ageing makes it difficult to diagnose the disease at its initial stage. Proper diagnosis of the disease happens only at a later stage when significant amount of neurons have already been impaired, thus making the disease control even more challenging.

Some of the genetic risk factors have been identified for Parkinson's disease, although their occurrence is very rare. Also, the risk of the disease associated to each of these genetic variations is very small. Other than genetic factors, exposure to some toxins and environmental factors has been suggested to be risk factors of PD, although again with a low correlation.

SUMMARY

Embodiments of the present disclosure present technological improvements as solutions to one or more of the above-mentioned technical problems recognized by the inventors in conventional systems. For example, in one embodiment, a system for risk assessment of Parkinson's disease in an individual has been provided. The system comprises a sample collection module, a DNA extractor, a sequencer, one or more hardware processors and a memory. The sample collection module obtains a sample from a body site of the individual. The DNA extractor extracts Deoxyribonucleic Acid (DNA) from the obtained sample. The sequencer sequences the isolated DNA using a sequencer to obtain stretches of DNA sequences. The memory in communication with the one or more hardware processors, wherein the one or more first hardware processors are configured to execute programmed instructions stored in the memory, to: analyze the stretches of DNA sequences to identify a plurality of bacterial taxa present in the sample, wherein the analysis results in the generation of a bacterial abundance profile having a bacterial abundance value of each of the plurality of bacterial taxa in the sample; preprocess the bacterial abundance profile to obtain scaled bacterial abundance values of the bacterial abundance profile; evaluate a score for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix; calculate a metabolic potential (MP) corresponding to each compound of the set of neuroactive compounds using the bacteria function matrix and the scaled bacterial abundance values, wherein the metabolic potential (MP) is indicative of the capability of the bacterial community for producing the neuroactive compound; generate a binary classification model utilizing the metabolic potential (MP) of each compound of the set of neuroactive compounds using machine learning techniques; predict the risk of the individual to develop or suffering from Parkinson's disease in a risk or no risk, using the binary classification model based on a predefined set of conditions; and design therapeutic approaches, through targeting the bacterial groups that are capable of producing a set of neurotoxic compounds or facilitating growth of healthy microbes, wherein the set of neurotoxic compounds are compounds which negatively affects the functioning of the gut-brain axis.

In another aspect, a method for risk assessment of Parkinson's disease in an individual has been provided. Initially, a sample is obtained from a body site of the individual. The Deoxyribonucleic Acid (DNA) is then extracted from the obtained sample. Further, the isolated DNA sequenced using a sequencer to obtain stretches of bacterial DNA sequences. Further, the stretches of DNA sequences are analyzed to identify a plurality of bacterial taxa present in the sample, wherein the analysis results in the generation of a bacterial abundance profile having a bacterial abundance value of each of the plurality of bacterial taxa in the sample. In the next step, the bacterial abundance profile is pre-processed to obtain scaled bacterial abundance values of the bacterial abundance profile. Further, a score is evaluated for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix. Later, a metabolic potential (MP) is calculated corresponding to each compound of the set of neuroactive compounds using the bacteria function matrix and the scaled bacterial abundance values, wherein the metabolic potential (MP) is indicative of the capability of the bacterial community for producing the neuroactive compound. In the next step, a binary classification model is generated utilizing the metabolic potential (MP) of each compound of the set of neuroactive compounds using machine learning techniques. Further, the risk of the individual to develop or suffering from Parkinson's disease in a risk or no risk is predicted, using the binary classification model based on a predefined set of conditions. And finally, therapeutic approaches are designed, through targeting the bacterial groups that are capable of producing a set of neurotoxic compounds or facilitating growth of healthy microbes, wherein the set of neurotoxic compounds are compounds which negatively affects the functioning of the gut-brain axis.

In yet another aspect, one or more non-transitory machine readable information storage mediums comprising one or more instructions which when executed by one or more hardware processors cause risk assessment of Parkinson's disease in an individual. Initially, a sample is obtained from a body site of the individual. The Deoxyribonucleic Acid (DNA) is then extracted from the obtained sample. Further, the isolated DNA is sequenced using a sequencer to obtain stretches of bacterial DNA sequences. Further, the stretches of DNA sequences are analyzed to identify a plurality of bacterial taxa present in the sample, wherein the analysis results in the generation of a bacterial abundance profile having a bacterial abundance value of each of the plurality of bacterial taxa in the sample. In the next step, the bacterial abundance profile is pre-processed to obtain scaled bacterial abundance values of the bacterial abundance profile. Further, a score is evaluated for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix. Later, a metabolic potential (MP) is calculated corresponding to each compound of the set of neuroactive compounds using the bacteria function matrix and the scaled bacterial abundance values, wherein the metabolic potential (MP) is indicative of the capability of the bacterial community for producing the neuroactive compound. In the next step, a binary classification model is generated utilizing the metabolic potential (MP) of each compound of the set of neuroactive compounds using machine learning techniques. Further, the risk of the individual to develop or suffering from Parkinson's disease in a risk or no risk is predicted, using the binary classification model based on a predefined set of conditions.

And finally, therapeutic approaches are designed, through targeting the bacterial groups that are capable of producing a set of neurotoxic compounds or facilitating growth of healthy microbes, wherein the set of neurotoxic compounds are compounds which negatively affects the functioning of the gut-brain axis.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Glossary— Terms Used in the Embodiments

The expression "microbiome" or "microbial genome" in the context of the present disclosure refers to the collection of genetic material of a community of microorganism that inhabit a particular niche, like the human gastrointestinal tract.

The expression "neuroactive compound" in the context of the present disclosure refers to the compounds that have the capability to regulate/interfere with neurotransmission, thus affecting brain function.

Figure 1:
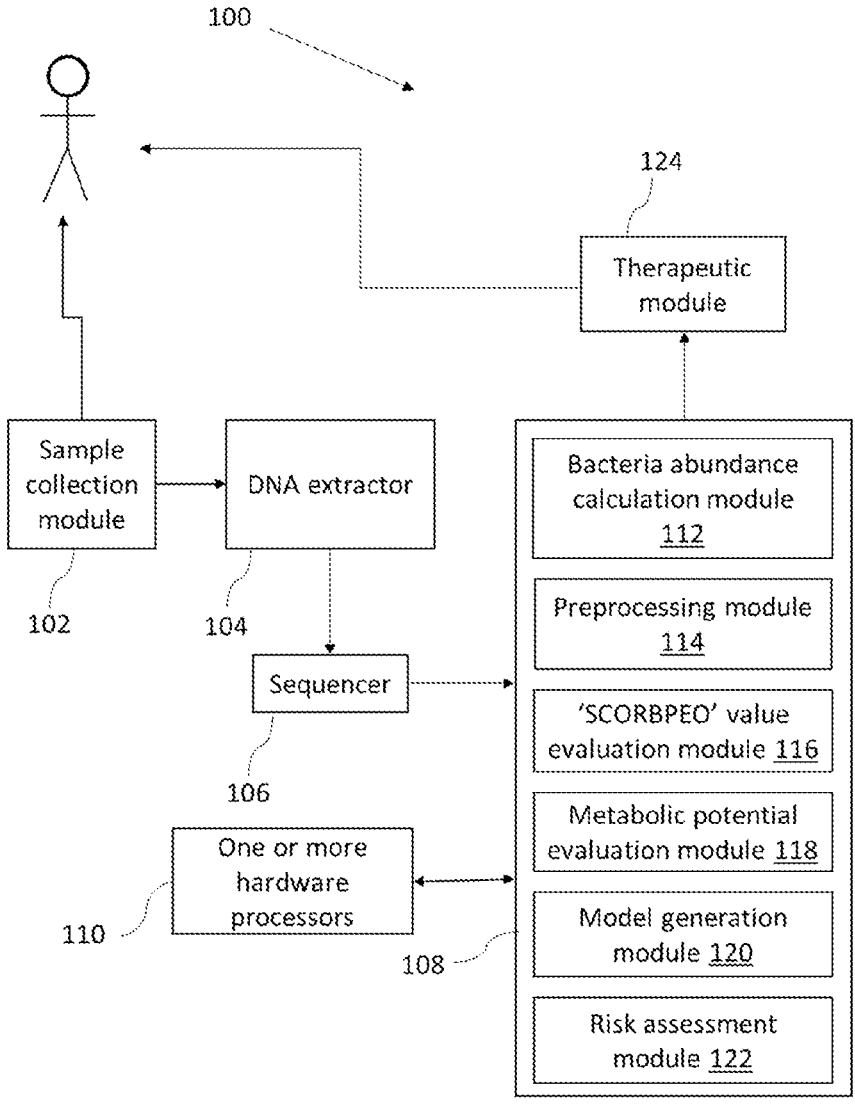
FIG. 1 illustrates a block diagram of a system for risk assessment of an individual for Parkinson's disease according to an embodiment of the present disclosure.
Figure 3:
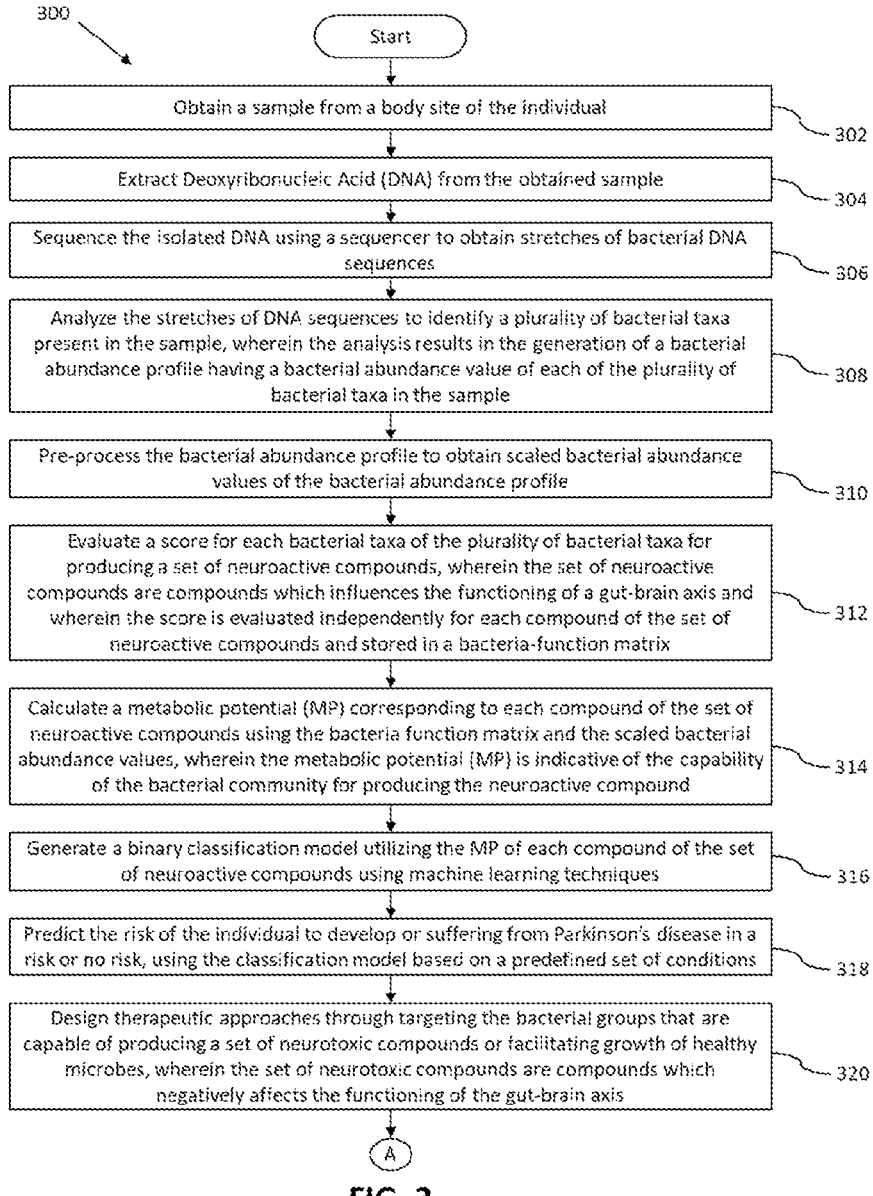
FIG. 3 is a flowchart illustrating the steps involved in risk assessment of an individual for Parkinson's disease according to an embodiment of the present disclosure.

Referring now to the drawings, and more particularly to FIG. 1 and FIG. 3, where similar reference characters denote corresponding features consistently throughout the figures, there are shown preferred embodiments and these embodiments are described in the context of the following exemplary system and/or method.

According to an embodiment of the disclosure, a system 100 for risk assessment of an individual for Parkinson's disease (PD) is shown in the block diagram of FIG. 1. The system 100 is using a non-invasive method for risk assessment of PD through prediction of metabolic potential of the bacteria residing in gastrointestinal tract (gut) of the individual. It should be appreciated that the system 100 is not limited to only bacteria in the gut, other microbes in the gut can also be considered for diagnosis and risk assessment of the individual having PD. Further, the present disclosure also provides microbiome based therapeutic approaches that can potentially minimize the side effects through maintaining the healthy cohort of bacteria in gut.

The system 100 is configured to calculate a score, named as 'SCORBPEO' (Score for Bacterial Production of Neuroactive Compounds) is evaluated from the gut bacterial taxonomic abundance profile, which is indicative of its metabolic potential for production of a particular neuroactive compound. It should be appreciated that the score can also be calculated using the abundances of other types of microorganisms. This score is subsequently used to assess the probability or risk of an individual of being affected by PD. Given the asymptomatic nature of the disease, the proposed non-invasive approach, if included as a part of routine health screening measures of individual above a certain age, can potentially help in early diagnosis of the PD. The system 100, in addition, entails therapeutic regimes through targeting the bacterial groups (residing in gut) that are capable of producing neurotoxic compounds or facilitating growth of healthy microbes (Including those producing neuro-protective compounds), wherein neuro-protective compounds refer to the compounds which positively affect the functioning of gut-brain axis.

In the present disclosure, a set of metabolic pathways harboured by the bacterial community residing in gut has been utilized to develop a PD diagnosis scheme that, when applied with the conventional screening tests, may help in early diagnosis of the PD. The set of metabolic pathways utilized in the current invention pertain to degradation of four amino acids (tryptophan, glutamate, and cysteine) leading to production of a set of neuroactive compounds. The set of neuroactive compounds include metabolites of tryptophan metabolism, namely, kynurenine, quinolinate, indole, indole acetic acid (IAA), Indole propionic acid (IPA), and tryptamine; a compound of glutamate metabolism—Gamma-amino butyric acid (GABA); and a compound produced through cysteine metabolism—Hydrogen sulfide ($H_2S$). Since, the microbiome's metabolic repertoire is a deeper reflector of the host-microbiome interplay than only the taxonomic groups, analysis of metabolomics of the resident microbiome is increasingly being acknowledged for understanding 'disease-microbiome' association.

According to an embodiment of the disclosure, the system 100 consists of a sample collection module 102, a DNA extractor 104, a sequencer 106, a memory 108 and a processor 110 as shown in FIG. 1. The processor 110 is in communication with the memory 108. The processor 110 is configured to execute a plurality of algorithms stored in the memory 108. The memory 108 further includes a plurality of modules for performing various functions. The memory 108 may include a bacterial abundance calculation module 112, a pre-processing module 114, a score evaluation module 116, a metabolic potential (MP) evaluation module 118, a model generation module 120 and a diagnosis and risk assessment module 122. The system 100 further comprises a therapeutic module 124 as shown in the block diagram of FIG. 1.

According to an embodiment of the disclosure, the bacterial sample is collected using the sample collection module 102. The sample collection module 102 is configured to collect the bacterial sample in the form of saliva/stool/blood/tissue/other body fluids/swabs from at least one body site/location viz. gut, oral, skin, or urinogenital tract etc. Normally, the sample is collected from an individual of age more than 50 years. The sample collection module 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The system 100 further comprises the DNA extractor 104 and the sequencer 106. DNA (Deoxyribonucleic acid) is first extracted from the microbial cells constituting the bacterial sample using laboratory standardized protocols by employing the DNA extractor 104. DNA isolation process using standard protocols based on the isolation kits (like Norgen, Purelink, OMNIgene/Epicentre etc.). Next, sequencing is performed using the sequencer 106. The isolated bacterial DNA, after purification is subjected to NGS (Next Generation Sequencing) technology for generating human readable form of short stretches of DNA sequence called reads. The said NGS technology involves amplicon sequencing targeting bacterial marker genes (such as 16S rRNA, 23S rRNA, rpoB, cpn60 etc.). The sequence reads, thus obtained, are computationally analysed through widely accepted standard frameworks for NGS data analysis. In another embodiment, the sequencer 106 may involve Whole Genome Sequencing (WGS) where the reads are generated for the total DNA content of a given sample. In yet another embodiment, the set of bacterial genes involved in the production of the neuroactive compounds (under the current invention) may be sequenced using targeted PCR (Polymerase Chain Reaction). In yet another implementation, RNA-seq. technology may be used to sequence the bacterial RNA (Ribonucleic acid) content of a given sample. This can be performed targeting the whole bacterial RNA content or a particular set of RNAs. RNA-seq provides insights into the active genes in a sample. In the current invention, RNA-seq may be performed targeting the RNAs (or transcripts) corresponding to the set of genes. The extracted and sequenced DNA sequences are then provided to the processor 110.

According to an embodiment of the disclosure, the further comprises the bacterial abundance calculation module 112. The bacterial abundance calculation module 112 is configured to analyze the stretches of DNA sequences to identify a plurality of bacterial taxa present in the sample, wherein the analysis results in the generation of a bacterial abundance profile having a bacterial abundance value of each of the plurality of bacterial taxa in the sample. The generation of bacterial abundance profile involves computationally analyzing one or more of a microscopic imaging data, a flow cytometry data, a colony count and cellular phenotypic data of microbes grown in in-vitro cultures, a signal intensity data, wherein these data are obtained by applying one or more of techniques including culture dependent methods, one or more of enzymatic or fluorescence assays, one or more of assays involving spectroscopic identification and screening of signals from complex microbial populations.

It should be appreciated that the bacterial abundance module 112 is not limited to only bacteria in the gut, other microbes in the gut can also be considered for analysis. The bacterial abundance calculation module 112 utilizes widely accepted methods/similar frameworks for calculation of abundance profile. The raw abundance profile, thus obtained, is further processed to obtain the relative abundance (RA) of each of the bacterial taxa. It should be appreciated that the taxa or taxon refers to individual taxonomic groups. Each characterized microbe from the sample can be associated to a taxonomic group. The methodology for calculation of relative abundance (RA) has been provided in the later part of the disclosure. In the present disclosure, the abundances of the bacterial groups at the taxonomic level of 'genus' have been considered. n another embodiment, the abundances of bacterial groups corresponding to other taxonomic levels such as, but not limited to, phylum, class, order, family, species, strain, OTUS (Operating Taxonomic Units), Asvs (Amplicon sequence variant) etc. may be considered. In another embodiment, other microorganisms (other than bacteria) may also be considered.

According to an embodiment of the disclosure, the memory 108 also comprises the pre-processing module 114. The pre-processing module is configured to pre-process the bacterial abundance profile to obtain normalized/scaled bacterial abundance values of the bacterial abundance profile. The pre-processing of the microbial abundance data comprises normalizing to represent the abundance in form of scaled values, wherein the normalization on microbial counts is performed through one or more of a rarefaction, a quantile scaling, a percentile scaling, a cumulative sum scaling or an Aitchison's log-ratio transformation.

Figure 2A:
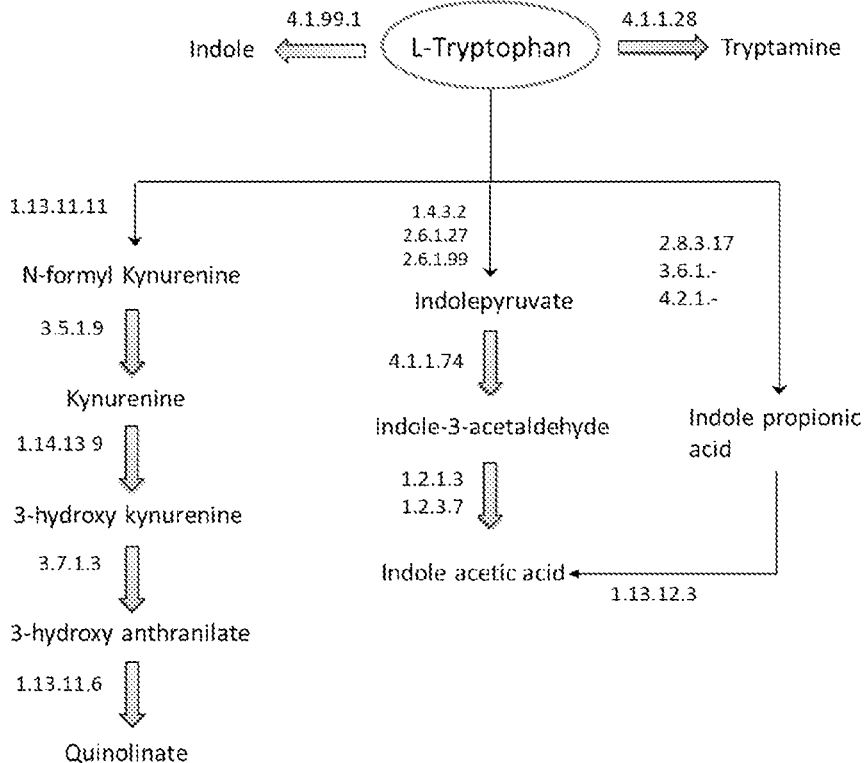
FIG. 2A-2C depicts the biochemical pathways for production of the eight neuroactive compounds in bacteria according to an embodiment of the disclosure.
Figure 2B:
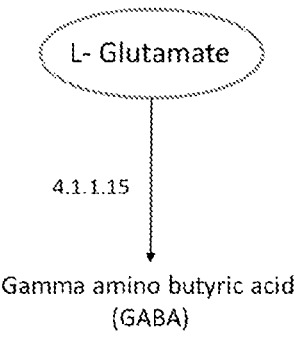
Figure 2C:
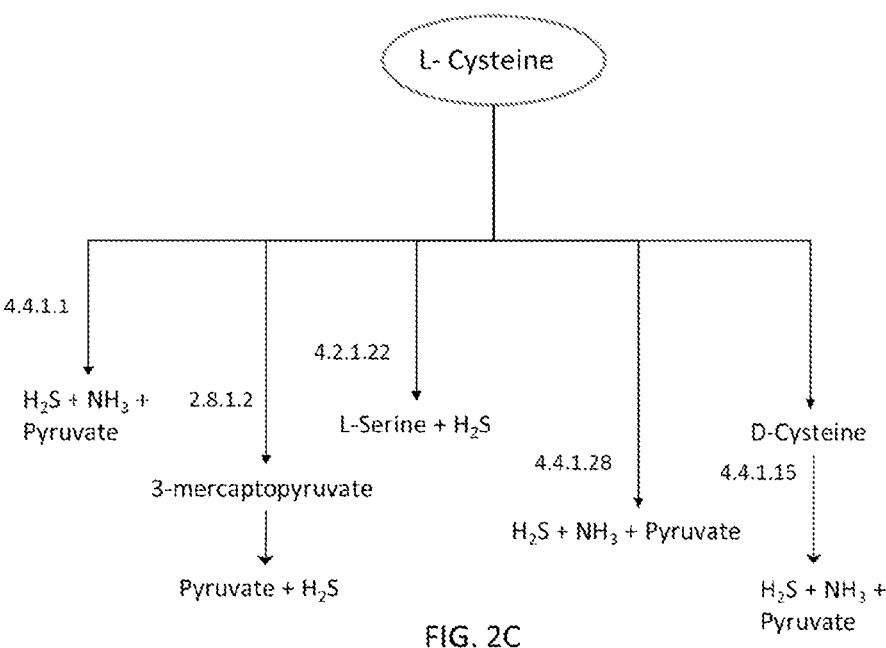

According to an embodiment of the disclosure, the memory 108 further comprises the score evaluation module 116. The score evaluation module 116 is configured to evaluate a score for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix. The gut-brain axis (GBA) refers to a bi-directional link between the central nervous system (CNS) and the enteric nervous system (ENS). The GBA enables communication of emotional and cognitive centres of the brain with peripheral intestinal functions. This communication primarily involves neural, endocrine and immune pathways. The set of neuroactive compounds include eight metabolites, including six metabolites of tryptophan metabolism, namely, kynurenine, quinolinate, indole, indole acetic acid (IAA), Indole propionic acid (IPA), and tryptamine; a compound of glutamate metabolism—Gamma-amino butyric acid (GABA); and a compound produced through cysteine metabolism—Hydrogen sulfide (H₂S). The biochemical pathways for production of the six compounds (through tryptophan utilization) in bacteria are depicted in FIG. 2A. The biochemical pathway for production of GABA through L-glutamate is shown in FIG. 2B. And, the biochemical pathway for the utilization of L-Cysteine is shown in FIG. 2C. It should be appreciated that the function association matrix can also be made using other microorganisms in the gut.

In an example, the score can be referred as the "SCORBPEO (Score for Bacterial Production of Neuroactive Compounds)" value. The set of neuroactive compounds include (but not limited to) Kynurenine, Quinolinate, Indole, Indole Acetic Acid (IAA), Tryptamine, Gamma-amino butyric acid (GABA) and Hydrogen sulfide (H₂S).

The 'SCORBPEO ((Score for Bacterial Production of Neuroactive Compounds)' value for a particular neuroactive compound 'i' corresponding to a bacterial genus T, was calculated using the equation (1)

$$SCORBPEO_{ij} = P * \alpha * \beta \qquad (1)$$

where P represents the proportion of strains belonging to the genus 'j' that have been predicted with compound 'i' producing capability (value of P ranges between '0' and '1'). Prediction of compound 'i' producing capability involves computational identification of the enzymes (proteins) involved in conversion of tryptophan to compound 'i'. Identification of enzymes was performed using widely accepted tools/packages (such as, but not limited to, Blast, HMMER, Pfam, etc.) which employ protein sequence/functional domain similarity search algorithms. Further, in order to increase the prediction efficiency, a filtration step was included (wherever applicable) based on presence of the genes/functional domains (of a particular pathway) in proximity to each other in the genome of a particular organism. α denotes a confidence value of the corresponding bacterial group. In an embodiment, the value of α ranges between '1' and '10'. It should be appreciated that the value may vary in another embodiments. β corresponds to a 'gut weightage' which represents an enrichment value of a particular pathway in the gut environment. In an embodiment, the value of β ranges between '1' and '5'. It should be appreciated that the value may vary in another embodiments. This value is calculated considering the number of gut-strains with capability of producing 'i' as compared to the number of corresponding non-gut strains.

In another example, computational identification of enzymes can also be performed using any one or a combination of gene/protein sequence similarity search algorithms, gene' protein sequence composition based algorithms, protein domain/motif similarity search algorithms, protein structure similarity search algorithms. The enzymes, thus obtained, may further be filtered using any one or a combination of genomic proximity analysis, functional association analysis, catalytic site analysis, sub-cellular localization prediction and secretion signal prediction. Further, identification of enzyme can also be performed using lab experiments which involves enzyme characterization assays.

Thus, in the current example, the values of the computed 'SCORBPEO' scores ranged between 0 and 50. The values were further rescaled to '0-10'. The range of 'SCORBPEO' value and the scaling may vary in another embodiment. For a particular pathway, a bacterial taxon having a higher 'SCORBPEO' would indicate a greater probability of production of a particular compound as compared to a taxon with a lower 'SCORBPEO'.

According to an embodiment of the disclosure, the memory 108 further comprises the metabolic potential (MP) evaluation module 118. The metabolic potential evaluation module 118 is configured to calculate a metabolic potential (MP) corresponding to each compound of the set of neuroactive compounds using the bacteria function matrix and the normalized/scaled bacterial abundance values, wherein the metabolic potential (MP) is indicative of the capability of the bacterial community (derived from the sequence data of the extracted DNA) for producing the neuroactive compound. The set of neuroactive compounds include six metabolites of tryptophan metabolism, namely, kynurenine, quinolinate, indole, indole acetic acid (IAA), Indole propionic acid (IPA), and tryptamine; a compound of glutamate metabolism—Gamma-amino butyric acid (GABA); and a compound produced through cysteine metabolism—Hydrogen sulfide (H₂S). The metabolic potential (MP) for production of a particular metabolite (by the bacterial community of interest) is calculated based on— (i) the relative abundance of the bacterial genera predicted to have the corresponding metabolic pathway and (ii) a predefined score referred to as (in the current invention) 'SCORBPEO' which represents the potential of a particular genus for production of the metabolite. Thus, the MP for production of a particular metabolite by the bacterial community (of interest) can be written as follows in equation (2). The equation (2) has been provided for the calculation of metabolic potential (MP) for Kynurenine.

$$MP_{Kyn} = \sum_{i=1}^{n} RA_i \times SCORBPEO_{[Kyn][i]} \qquad (2)$$

Where, $MP_{Kyn}$—Metabolic potential of the bacterial community of interest for the production of Kynurenine. The bacterial community, in the current invention, may indicate the one isolated from the gut sample of the individual.

n—Number of Kynurenine producing bacterial genera present in the bacterial community of interest. This number is acquired from the predefined 'bacteria-function matrix'. The methodology followed for construction of the 'bacteria-function matrix' has been explained in the later part of the disclosure with the help of experimental study.

RA—Relative abundance of a particular bacterial genus predicted to have the metabolic pathway for Kynurenine production. The 'RA' is calculated using the pre-processing module 114 as described above.

$SCORBPEO_{[Kyn][i]}$—The potential of genus 'i' for production of Kynurenine as explained earlier 'SCORBPEO' score or any other score related to microbial production of any other products/by-products of amino acid metabolism (apart from the above mentioned eight compounds) for risk assessment/diagnosis/therapeutics of Parkinson's disease are well within the scope of the present disclosure.

Thus, in the present embodiment, the MP is calculated for eight neuroactive compounds, i.e. for Kynurenine, Quinolinate, Indole, Indole Acetic Acid (IAA), Indole propionic acid (IPA), Tryptamine, GABA and $H_2S$. These eight 'MP' values are used further. In an example, the values of the computed MP scores ranges between 0 and 50. Though it should be appreciated that the range of MP values may vary in other examples. The values were further rescaled to '0-10'. For a particular pathway, a bacterial taxon having a higher MP would indicate a greater capability of production of a particular compound as compared to a taxon with a lower MP.

It should be appreciated that the MP score or any other score related to microbial production of any other products/by-products of amino acid metabolism (apart from the above mentioned eight compounds) for risk assessment/diagnosis/therapeutics of Parkinson's disease are well within the scope of the present disclosure.

According to an embodiment of the disclosure, the memory 108 further comprises the model generation module 120. The model generation module 120 is configured to generate a binary classification model utilizing the MP of each of the plurality of compounds using machine learning techniques. In an embodiment, generating the binary classification model using machine learning techniques may be performed using one or more of classification algorithms which include random forest, decision trees, linear regression, logistic regression, naive Bayes, linear discriminant analyses, k-nearest neighbour algorithm, Support Vector Machines and Neural Networks. The model generation module 120 builds the binary classification model for diagnosis of PD or for predicting the risk of an individual to be suffering from PD.

A model for diagnosis/risk assessment of Parkinson's disease (PD) is generated based on the 'Metabolic potential (MP)' values corresponding to each of the eight neuroactive compounds. These compounds include (but not limited to) Kynurenine, Quinolinate, Indole, Indole acetic acid (IAA), Indole propionic acid (IPA), Tryptamine, Gamma-amino butyric acid (GABA), and Hydrogen sulfide ($H_2S$). The 'MP' score or any other score related to microbial production of any other products/by-products of amino acid metabolism (apart from the above mentioned eight compounds) for risk assessment/diagnosis/therapeutics of PD are well within the scope of the present invention. The publicly available gut microbiome dataset (16S sequence) pertaining to PD patients and age-matched healthy controls were used to validate the efficiency of the PD risk assessment scheme proposed in the present disclosure.

According to an embodiment of the disclosure, the memory 108 also comprises the diagnosis and risk assessment module 122. The diagnosis and risk assessment module 122 is configured to predict the probability of the individual for PD or risk of development of PD in one of a probability/risk or a no probability/risk, using the binary classification model based on a predefined set of conditions. The prediction outcome of the risk assessment module 120 indicates the risk of disease development. For another category of individuals with one or more of the associated symptoms, the risk assessment module 120 can be used as an initial non-invasive diagnostic measure. For a person (of age >=50 years) undergoing routine health check-up, especially those with genetic pre-disposition to the disorder or who are at exposure to environmental toxins, the prediction outcome of the current module indicates the risk of disease development. For another category of individuals with one or more of the associated symptoms, the current module can be used as a non-invasive diagnostic measure as an adjunct to the motor function screening i.e. commonly practiced.

The predefined set of condition comprises comparing the metabolic potential for production of one of the set of neuroactive compounds with a threshold value, wherein the result of comparison is: no risk of Parkinson's disease if the metabolic potential is less than or equal to the threshold value, or the significant risk of Parkinson's disease if the metabolic potential is more than the threshold value.

According to an embodiment of the disclosure, the system 100 also comprises the therapeutic module 124. The therapeutic module 124 is configured to design therapeutic approaches, through targeting the bacterial groups that are capable of producing a set of neurotoxic compounds or facilitating growth of healthy microbes, wherein the set of neurotoxic compounds are compounds which negatively affects the functioning of the gut-brain axis. The therapeutic module 124 involves identification of a consortium of microbes which can be used (in form of pre-/probiotic/synbiotic) in order to—(i) reduce the growth of bacteria (in the gut) which are capable of producing neurotoxic compounds and (ii) enhance the growth of beneficial bacteria (in the gut) which can help maintaining a healthy gut or produce neuroactive compounds which are beneficial for functioning and regulation of gut-brain axis. This consortium of microbes can be administered either alone or as an adjunct to the conventional antibiotic drugs for improved treatment of PD and for the gastrointestinal problems associated to PD. In the present embodiment, identification of the consortium of microbes (bacteria) is performed based on the MP values of the bacterial genera identified in a particular sample. Though it should be appreciated that the MP values of other microorganisms can also be considered.

In operation, a flowchart 300 illustrating the steps involved for risk assessment of an individual for Parkinson's disease (PD) is shown in FIG. 2A-2B. Initially at step 302, a sample is obtained from the body site of the individual. At step 304, extracting Deoxyribonucleic Acid (DNA) from the obtained sample. Further at step 306, the isolated DNA is sequenced using a sequencer to obtain stretches of DNA sequences. In the next step 308, the stretches of DNA sequences are analyzed to identify a plurality of bacterial taxa present in the sample, wherein the analysis results in the generation of a bacterial abundance profile having a bacterial abundance value of each of the plurality of bacterial taxa in the sample. Further at step 310, the bacterial abundance profile is pre-processed to obtain normalized/scaled bacterial abundance values of the bacterial abundance profile.

In the next step 312, the score is evaluated for each bacterial taxa of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix. At step 314, the metabolic potential (MP) corresponding to each compound of the set of neuroactive compounds is calculated using the bacteria function matrix and the scaled bacterial abundance values, wherein the metabolic potential (MP) is indicative of the capability of the bacterial community for producing the neuroactive compound.

At step 316, the binary classification model is generated utilizing the metabolic potential (MP) of each compound of the set of neuroactive compounds using machine learning techniques. At step 318, the risk of the individual to develop or suffering from Parkinson's disease in a risk or no risk is predicted, using the binary classification model based on a predefined set of conditions. And finally at step 320, therapeutic approaches are designed, through targeting the bacterial groups that are capable of producing a set of neurotoxic compounds or facilitating growth of healthy microbes, wherein the set of neurotoxic compounds are compounds which negatively affects the functioning of the gut-brain axis.O According to an embodiment of the disclosure, the system 100 for diagnosis and risk assessment of the individual for Parkinson's disease (PD) can also be explained with the help of following example.

The prediction of the bacterial community's metabolic potential for the production of neuroactive compounds requires the (bacterial) taxonomic abundance data, generated using one of the state-of-art algorithms, as an input. An example of the bacterial taxonomic abundance data (obtained from the published study) has been shown below (Table 1). Microbiome data pertaining to a total of 74 Parkinson samples and corresponding 74 healthy samples are provided in the study. Table 1 shows a subset of the bacterial taxonomic abundance at genera level corresponding to one Parkinson and one healthy sample.

TABLE 1

Subset of bacterial genera abundance obtained through analysing gut microbiome data corresponding to an individual with Parkinson's disease (PD) and a healthy control.

| Bacterial Taxa (Genera) | PD Sample | Control Sample |
|---|---|---|
| Bacteroides | 552 | 124 |
| Faecalibacterium | 33 | 124 |
| Roseburia | 43 | 33 |

TABLE 1-continued

Subset of bacterial genera abundance obtained through analysing gut microbiome data corresponding to an individual with Parkinson's disease (PD) and a healthy control.

| Bacterial Taxa (Genera) | PD Sample | Control Sample |
|---|---|---|
| Oscillibacter | 161 | 32 |
| Coprococcus | 8 | 25 |
| Parabacteroides | 0 | 41 |
| Dialister | 89 | 0 |
| Lachnospiracea_incertae_sedis | 21 | 189 |
| Fusicatenibacter | 2 | 23 |
| Ruminococcus | 7 | 8 |
| Alistipes | 108 | 6 |

The raw bacterial abundance data was then normalized to represent the relative abundance values. It should be noted that the use of any kind of normalization or scaling of bacterial abundance values, including percentage, cumulative sum scaling, minmax scaling, maxAbs scaling, robust scaling, percentile, quantile, Atkinson's log transformation, etc. is well within the scope of this disclosure. Further the percentage-normalized abundance data was pre-processed to remove bacterial genera which had missing/null values in at-least 70% of the samples analysed. The objective of this exercise was to cleanse the data and remove inconsistencies in the data before constructing a model. Further, the pre-processed data was transformed by scaling from 0 to 1. This was done so that the abundances of bacterial genera in different samples are placed at a common scale. Table 2 shows the values of the scaled bacterial abundance data of the above-mentioned raw abundance data (Table 1).

TABLE 2

Scaled values of the bacterial abundances shown in Table 1

| Taxa | PD Sample | Control Sample |
|---|---|---|
| Bacteroides | 1 | 1 |
| Faecalibacterium | 0.059 | 0.39 |
| Roseburia | 0.077 | 0.106 |
| Oscillibacter | 0.291 | 0.102 |
| Coprococcus | 0.014 | 0.08 |
| Parabacteroides | 0 | 0.131 |
| Dialister | 0.161 | 0 |
| Lachnospiracea_incertae_sedis | 0.038 | 0.607 |
| Fusicatenibacter | 0.003 | 0.073 |
| Ruminococcus | 0.012 | 0.025 |
| Alistipes | 0.195 | 0.019 |

The transformed/scaled bacterial abundance values were then used to evaluate the score referred to as 'Metabolic potential (MP)' in the present disclosure.

The identification of consortium of microbes that can potentially facilitate improved therapy of Parkinson's disease (PD) is performed based on the following two aspects— (i) differentially abundant microbial taxa in cohorts of PD patients and healthy individuals and (ii) the 'SCORBPEO' values of the differentially abundant taxa corresponding to the production of neuroactive compounds under the present disclosure.

The abundant genera in healthy cohort which are not able to produce any neurotoxic compound may help maintaining a 'healthy' microbiome in gut and thus might aid in prevention or alleviating symptoms of PD. These genera are listed in Table 3. Any pre/probiotic/synbiotic formulation which facilitates growth of the above mentioned healthy microbiome can also be used as a therapeutic adjunct for PD. The differentially abundant taxa (genera in the current invention) in healthy cohort were identified using state-of-art statistical test

TABLE 3

Differentially abundant genera in healthy cohort lacking
pathways for production of any neuro-toxic compound

| Genera | p-value |
| --- | --- |
| *Alloprevotella* | 0.03 |
| *Butyricicoccus* | 0.02 |
| *Prevotella* | 0.002 |
| *Roseburia* | 0.01 |
| *Succinispira* | 0.02 |

The proposed probiotic formulation may be composed of bacterial strains belonging to the genera listed in Table 3. The strains with known beneficial effects (like butyrate production etc.) are most probable candidates for probiotic formulation. For example, certain strains under the genera *Roseburia* and *Butyricicoccus* have been reported to have beneficial role in the gut. Thus, these strains may be provided as probiotic formulation in order to alleviate the symptoms of PD through maintaining a healthier gut microbiome, thus improving the efficiency of current therapeutic approaches or minimizing the side effects of the conventional therapies of PD. The proposed probiotic strains can thus be utilized as an adjunct therapy for PD. The bacterial strains belonging to the genera *Roseburia* and *Butyricicoccus* that are commonly found in gut, are listed in Table 4.

TABLE 4

Bacterial strains belonging to the genera *Roseburia* and
*Butyricicoccus*, which are commonly found in gut (obtained
from 'NIH Integrative Human Microbiome Project')

| Genus | Strain |
| --- | --- |
| *Roseburia* | *Roseburia_intestinalis_L1-82* |
| | *Roseburia_intestinalis_M50_1* |
| | *Roseburia_intestinalis_XB6B4* |
| | *Roseburia_inulinivorans_DSM_16841* |
| *Butyricicoccus* | *Butyricicoccus_pullicaecorum_1* |

Table 5 below shows the summary of the publicly available dataset used for validation of the proposed methodology. The dataset involves publicly available gut microbiome sequence data samples from 74 individuals suffering from PD and corresponding 74 healthy controls from Finnish population. The 16S rRNA data from the study was analysed in in order to obtain the 'MP' values for the eight neuroactive compounds under the invention. These values corresponding to a subset of samples from the study is provided in Table 6.

TABLE 5

Summary of the publicly available dataset used
for validation of the proposed methodology

| Sample type | Data type | No. of PD patients | No. of healthy individuals |
| --- | --- | --- | --- |
| Fecal sample | 16S rRNA sequence read | 74 | 74 |

TABLE 6

'Metabolic potential (MP)' values corresponding to the eight neuro-active
compounds evaluated for a subset of microbiome samples mentioned from the study.

| | Kynurenine | Quinolinate | IAA | IPA | Indole | Tryptamine | GABA | $H_2S\_1$ | $H_2S\_2$ | $H_2S\_3$ | $H_2S\_4$ | $H_2S\_5$ |
| --- | --- | --- | --- | --- | --- | --- | --- | --- | --- | --- | --- | --- |
| PD_1 | 0 | 0 | 0.33 | 0 | 4.64 | 0.16 | 4.29 | 0 | 0.08 | 1.23 | 0.02 | 0 |
| PD_2 | 0 | 0 | 0.12 | 0 | 4.15 | 0.09 | 4.17 | 0 | 0.09 | 0.58 | 0.02 | 0 |
| Healthy_1 | 0 | 0 | 0 | 0 | 2.01 | 0.75 | 1.34 | 0 | 0 | 0.86 | 0 | 0 |
| Healthy_2 | 0 | 0 | 0 | 0 | 1.81 | 0.03 | 1.79 | 0 | 0 | 1.03 | 0 | 0 |

$H_2S\_1$, $H_2S\_2$, $H_2S\_3$, $H_2S\_4$ and $H_2S\_5$ represent the pathways involving 3-mercaptopyruvate sulfurtransferase (EC: 2.8.1.2), cystathionine beta-synthase (EC: 4.2.1.22), cystathionine gamma lyase (EC: 4.4.1.1), D-cysteine desulfhydrase (EC: 4.4.1.15), and L-cysteine desulfhydrase (EC: 4.4.1.28) respectively.

A model for classification (disease or healthy) of the samples was generated using Random Forest classifier. The 'MP' values obtained for the above-mentioned eight metabolites were used as features for training the classifier. The sample set (74 PD samples and 74 Healthy samples) was randomly divided into training and testing set samples, in the ratio of 70:30 (70% of the samples as training set and the remaining 30% as the test set), such that the proportion of diseased and healthy samples remained equivalent in both training and test set. The training of the model was performed by utilizing the Random forest package v4.6 with 10-fold cross-validation in 10 replicates (i.e. 100 tests). The performance of the individual models obtained was evaluated with the 'area under curve' (AUC) of the 'receiver operating characteristics' (ROC) using the R pROC package. From each cross-validation fold, top 5 differentiating features were picked and 'giniscore' was utilized to rank them based upon their cumulative importance. Further, the ranked features were progressively added into the model, according to their cumulative importance ('giniscore') and the performance of the model was evaluated (in terms of AUC) after the addition of every new feature. A final 'bagged' RF model was obtained which utilized two most differentiating features. Out of the eight metabolites (mentioned in Table 6), a combination of 'GABA' and Indole (two most differentiating features) were observed to best classify/segregate healthy and diseased samples. The parameters showing the model efficiencies for training and test sets are provided below in table 7.

TABLE 7

Parameters showing model efficiency of classification based on the combination of 'MP' values

| Combination of features | Threshold used for testing (T) | Train sensitivity | Train specificity | Train accuracy | Train AUC | Test sensitivity | Test specificity | Test accuracy | Test AUC |
|---|---|---|---|---|---|---|---|---|---|
| GABA, Indole | 0.51751 | 70.58 | 70.58 | 70.58 | 75.37 | 73.91 | 60.86 | 67.39 | 74.007 |

The prediction of the risk of PD could be performed based on the combination of 'MP' values and a threshold value corresponding to the above-mentioned features 'GABA' and Indole according to the following rules—

$MP_{GABA, Indole} <= T$, indicates no risk of PD or no Parkinson disease, where T is the threshold value (as mentioned in the above table 7).

$MP_{GABA, Indole} > T$ indicates significant risk/probability of suffering from PD.

It may be noted that, the current invention primarily relies on the metabolic capability of the resident gut microbiota, which is known to differ in relation to not only the diseased state but also various other factors like dietary pattern, demography, lifestyle etc. Therefore, any other neuroactive compound(s) (or any other compound belonging to amino acid metabolism) either alone or in combination with one or more of the compounds under invention may prove to be efficient risk assessment factors for PD or any other neurological disease/disorder for individuals from a different geography or/and of different ethnicity/lifestyle.

Details on the bacterial genes involved in production of neuro-active compounds under the present disclosure for the risk assessment of Parkinson's disease is shown below in Table 8.

| Metabolic pathways | Gene name | Enzyme Id | Functional domain (obtained from Pfam database) |
|---|---|---|---|
| Tryptophan -> Kynurenine | kynA | 1.13.11.11 | Trp_dioxygenase |
| | kynB | 3.5.1.9 | Cyclase |
| Tryptophan -> Quinolinate | kynA | 1.13.11.11 | Trp_dioxygenase |
| | kynB | 3.5.1.9 | Cyclase |
| | kmo | 1.14.13.9 | FAD_binding_3 |
| | kynU | 3.7.1.3 | Aminotran_5 |
| | HAAO | 1.13.11.6 | 3-HAO |
| Tryptophan -> Indole | TnaA | 4.1.99.1 | Beta_elim_lyase |
| Tryptophan -> Indole acetic acid | ipdC | 4.1.1.74 | TPP_enzyme_C TPP_enzyme_M TPP_enzyme_N |
| | aldh | 1.2.1.3 | Aldedh |
| | AAO1 | 1.2.3.7 | Ald_Xan_dh_C Ald_Xan_dh_C2 |
| | iaaM | 1.13.12.3 | Amino_oxidase |
| Tryptophan -> Indole propionic acid | fldL | NA | AMP_binding AMP_binding_C |
| | fldA | 2.8.3.17 | CoA_transf_3 |
| | fldI | 3.6.1.— | BcrAD_BadFG |

16

-continued

| Metabolic pathways | Gene name | Enzyme Id | Functional domain (obtained from Pfam database) |
|---|---|---|---|
| | fldB | 4.2.1.— | HGD-D |
| | fldC | 4.2.1.— | HGD-D |
| Tryptophan -> Tryptamine | ddc | 4.1.1.28 | Pyridoxal_deC |

-continued

| Metabolic pathways | Gene name | Enzyme Id | Functional domain (obtained from Pfam database) |
|---|---|---|---|
| Glutamate -> Gamma amino butyric acid (GABA) | gadB, gadA | 4.1.1.15 | Pyridoxal_deC, AA_permease_2 |
| Cysteine -> H2S | CTH | 4.4.1.1 | PALP |
| | MPST | 2.8.1.2 | Rhodanese |
| | CBS | 4.2.1.22 | PALP, CBS |
| | — | 4.4.1.28 | SDH_alpha |
| | gadB, gadA | 4.4.1.15 | Pyridoxal_deC |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of accurate and early diagnosis of the Parkinson's disease. The embodiment provides a system and method for risk assessment of Parkinson's disease (PD) in the individual.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for risk assessment of Parkinson's disease in an individual, the method comprising:

obtaining a sample from a body site of the individual;

extracting Deoxyribonucleic Acid (DNA) from the obtained sample to obtain isolated DNA;

sequencing the isolated DNA using a sequencer to obtain stretches of bacterial DNA sequences;

analyzing, via one or more hardware processors, the stretches of DNA sequences to identify a plurality of bacterial taxa present in the sample, wherein the analysis results in the generation of a bacterial abundance profile having a bacterial abundance value of each of the plurality of bacterial taxa in the sample;

pre-processing, via the one or more hardware processors, the bacterial abundance profile to obtain scaled bacterial abundance values of the bacterial abundance profile;

evaluating, via the one or more hardware processors, a score for each bacterial taxon of the plurality of bacterial taxa for producing a set of neuroactive compounds, wherein the set of neuroactive compounds are compounds which influences the functioning of a gut-brain axis and wherein the score is evaluated independently for each compound of the set of neuroactive compounds and stored in a bacteria-function matrix, wherein the score (SCORBPEO) is calculated using formula:

$$SCORBPEO_{ij} = P * \alpha * \beta$$

where P—proportion of strains belonging to the genus 'j' that have been predicted with neuroactive compound 'i' producing capability, wherein prediction of the neuroactive compound 'i' producing capability involves computational identification of enzymes or proteins involved in conversion of tryptophan to the neuroactive compound 'i', wherein the identification of enzymes or proteins employ protein sequence or functional domain similarity search algorithms, wherein a filtration step is included based on presence of genes or functional domains of a particular pathway in proximity to each other in a genome of a particular organism to increase prediction efficiency, α—confidence value of the corresponding bacterial group, where the confidence value is evaluated based on the relative number of strains belonging to a particular genus, and β—'weightage' which represents an enrichment value of a particular pathway in a particular body site;

calculating, via the one or more hardware processors, a metabolic potential (MP) corresponding to each compound of the set of neuroactive compounds using the bacteria function matrix and the scaled bacterial abundance values, wherein the metabolic potential (MP) is indicative of the capability of the bacterial community for producing the neuroactive compound, wherein the metabolic potential (MP) is calculated using formula:

$$MP_{NAC} = \sum_{i=1}^{n} RA_i \times SCORBPEO_{[NAC][i]}$$

where, $MP_{NAC}$—Metabolic potential of the bacterial community (of interest) for production of a particular neuroactive compound, n—number of the particular neuroactive compound producing bacterial genera present in the bacterial community of interest, RA—relative scaled abundance of a particular bacterial genus 'i' predicted to have the metabolic pathway for the neuroactive compound production, and $SCORBPEO_{[NAC]\ [i]}$—The 'SCORBPEO (Score for Bacterial Production of Neuro-active Compound)' score of genus 'i' for production of the particular neuroactive compound 'NAC';

generating, via the one or more hardware processors, a binary classification model utilizing the metabolic potential (MP) of each compound of the set of neuro- active compounds using machine learning techniques, wherein MP values corresponding to the set of neuro- active compounds are considered as features for train- ing the binary classification model, wherein a sample set is randomly divided into training set samples and testing set samples, in a ratio such that a proportion of diseased and healthy samples remained equivalent in both training and test set, wherein the training of the binary classification model is performed by utilizing a random forest package with 10-fold cross-validation, wherein from each cross-validation fold, differentiating features are picked and a giniscore is utilized to rank the differentiating features based upon their cumulative importance, and the ranked differentiating features are progressively added into the binary classification model, based on their cumulative importance, wherein performance of the binary classification model is evalu- ated after addition of every new feature;

predicting, via the one or more hardware processors, the risk of the individual to develop or suffering from Parkinson's disease in a risk or no risk, using the binary classification model based on a predefined set of con- ditions, wherein the individual has the risk;

designing therapeutic approaches, through targeting the bacterial groups that are capable of producing a set of neurotoxic compounds or facilitating growth of healthy microbes, wherein the set of neurotoxic compounds are compounds which negatively affect the functioning of the gut-brain axis, wherein designing the therapeutic approaches includes identification of a consortium of microbes to be used in the form of prebiotic or probiotic or symbiotic to (i) reduce growth of bacteria in the gut which are capable of producing the set of neurotoxic compounds and (ii) enhance the growth of beneficial bacteria in the gut which is capable of maintaining a healthy gut or produce the set neuroactive compounds which are beneficial for functioning and regulation of the gut-brain axis, wherein the identification of the consortium of microbes is performed based on the MP values of a bacterial genera identified in the sample, differentially abundant bacterial taxa in cohorts of Parkinson's disease patients and healthy individuals and the SCORBPEO score values of the differentially abundant bacterial taxa corresponding to the production of the set of neuroac- tive compounds; and administering, to the individual with the risk, the designed consortium of microbes for improved treatment of Parkinson's disease, including minimization of side effects of therapeutic drugs through maintaining a healthy cohort of the bacteria in the gut, wherein the method is implemented for diagnosis or treatment of Parkinson's disease.

2. The method according to claim 1, wherein the pre- defined set of conditions comprises comparing the metabolic potential for production of one of the set of neuroactive compounds with a threshold value, wherein the result of comparison is:

no risk of Parkinson's disease if the metabolic potential is less than or equal to the threshold value, or a significant risk of Parkinson's disease if the metabolic potential is more than the threshold value.

3. The method according to claim 1, wherein isolating and sequencing stretches of DNA further comprises at least one of:

amplifying and sequencing bacterial 16S rRNA, 23S rRNA, rpoB, or cpn60 marker genes from the bacterial DNA, amplifying and sequencing one or more of a full-length or one or more specific regions of the bacterial 16S rRNA, 23S rRNA, rpoB, cpn60 marker genes from the micro- bial DNA, amplifying and sequencing one or more phylogenetic marker genes from the bacterial DNA, or whole genome shotgun sequencing (WGS) data corre- sponding to bacterial DNA, isolated from the body site of the individual.

4. The method according to claim 1, wherein the step of sequencing comprises one or more of: an amplicon sequenc- ing, a whole genome shotgun sequencing (WGS), a frag- ment library based sequencing technique, a mate-pair library or a paired-end library based sequencing technique, a poly- merase chain reaction (PCR), an RNA sequencing tech- nique, or a microarray-based technique.

5. The method according to claim 1, wherein the step of pre-processing the microbial abundance data comprises nor- malizing to represent the abundance in the form of scaled values, wherein the normalization on microbial counts is performed through one or more of a rarefaction, a quantile scaling, a percentile scaling, a cumulative sum scaling, or an Aitchison's log-ratio transformation.

6. The method according to claim 1 wherein the set of neuroactive compounds comprises one or more of Kynure- nine, Quinolinate, Indole, Indole acetic acid (IAA), Indole propionic acid (IPA), Tryptamine, Gamma-amino butyric acid (GABA), and Hydrogen sulphide ($H_2S$).

7. The method according to claim 1, wherein generating the binary classification model using machine learning tech- niques is performed using one or more of random forest, decision trees techniques, linear regression, logistic regres- sion, naive Bayes, linear discriminant analyses, k-nearest neighbour algorithm, Support Vector Machines, and Neural Networks techniques.

8. The method according to claim 1, wherein the sample is one of saliva, stool, blood, body fluid, tissue, or swab.

9. The method according to claim 1, wherein the body site is one of a gut, oral, skin, or urinogenital tract of the individual.

10. The method according to claim 1, wherein the healthy microbes include microbes producing neuro-protective com- pounds which have beneficial effects on the gut-brain axis.

11. The method according to claim 1, wherein values of the computed score is rescaled to 0-10, wherein for the particular pathway, a bacterial taxa having a higher SCORBPEO indicate a greater probability of production of a particular neuroactive compound as compared to a taxa with a lower SCORBPEO, wherein scaling of the bacterial abundance values is performed through one or more of: a percentage, a cumulative sum scaling, a minmax scaling, a maxAbs scaling, a robust scaling, a percentile, a quantile, or an Atkinson's log transformation, wherein percentage scaled bacterial abundance data is pre-processed to remove bacte- rial genera having missing or null values in the samples analyzed to cleanse the bacterial abundance data and remove inconsistencies in the bacterial abundance data before gen- erating the binary classification model and the pre-processed data is transformed by scaling from 0 to 1 such that the abundances of the bacterial genera in different samples are placed at a common scale.

12. The method according to claim 1, wherein the consortium of microbes is composed of a combination of GABA and Indole to classify healthy samples and diseased samples, wherein the bacterial strains belonging to genera *Roseburia* and *Butyricicoccus* are administered as probiotic formulation in order to alleviate symptoms of Parkinson's disease through maintaining a healthier gut microbiome, thereby improving an efficiency of current therapeutic approaches or minimizing the side effects of conventional therapies of Parkinson's disease.

\*   \*   \*   \*   \*